United States Patent [19]
Swiet

[11] Patent Number: 5,915,542
[45] Date of Patent: Jun. 29, 1999

[54] AMPHIBIOUS SPORT GOGGLE HAVING MALLEABLE FRAME AND INTERCHANGEABLE LENSES

[76] Inventor: Theodore L. Swiet, 2215 Bryant St., San Francisco, Calif. 94110

[21] Appl. No.: 08/788,514

[22] Filed: Jan. 24, 1997

[51] Int. Cl.$^6$ ........................................................ A61F 9/02
[52] U.S. Cl. ..................................... 2/441; 2/440; 351/43
[58] Field of Search ............................... 2/440, 441, 442, 2/443, 444, 445, 446, 431, 13, 438, 439, 428, 452; 351/43, 47, 59

[56] References Cited

U.S. PATENT DOCUMENTS

| | | | |
|---|---|---|---|
| 730,192 | 6/1903 | Moritz | 2/13 |
| 861,504 | 7/1907 | Cover | 2/440 |
| 1,514,943 | 11/1924 | Willson et al. | 2/444 |
| 1,565,890 | 12/1925 | Baker | 2/441 |
| 1,636,443 | 7/1927 | Schumacher | 2/441 |
| 1,850,812 | 3/1932 | Scharf | 2/440 |
| 2,321,159 | 6/1943 | Ryan | 2/441 |
| 2,373,388 | 4/1945 | Fischer | 2/440 |
| 3,122,962 | 3/1964 | DeAngelos | 2/441 |
| 3,440,662 | 4/1969 | O'Shea | 2/441 |
| 5,093,940 | 3/1992 | Nishiyama | 2/441 |
| 5,459,882 | 10/1995 | Yamamoto | 2/445 |

FOREIGN PATENT DOCUMENTS

| | | | |
|---|---|---|---|
| 576971 | 5/1924 | France | 2/441 |
| 13589 | 6/1907 | United Kingdom | 2/440 |
| 651467 | 4/1951 | United Kingdom | 2/440 |

*Primary Examiner*—Amy B. Vanatta
*Attorney, Agent, or Firm*—Haverstock & Owens LLP

[57] ABSTRACT

An amphibious sport goggle having a malleable frame and interchangeable lenses. The frame includes a pair of eye cups constructed of a soft, flexible and gas permeable material, preferably 4-way stretch "LYCRA" fabric. A lens is held in place across a first open end of each eye cup by pair of flexible rings sewn into the eye cup and oriented parallel to each other for retaining the lens therebetween. The lenses are interchangeable with lenses having various shapes, colors and optical properties. A third flexible ring is sewn into each eye cup around the perimeter of a second open end for providing additional structure to the eye cup and for providing a seal between the wearer's face and the eye cup. The rings are preferably rubber. An outer layer forms a sleeve around a portion of each eye cup. The sleeve is attached to the eye cup in the vicinity of the perimeter of the lens. The sleeve is constructed of a durable and flexible material, preferably "CORDURA" fabric. The eye cups are held together near the bridge of the wearer's nose, preferably by a short strap which is attached to each sleeve. An adjustable elastic strap is also attached to each sleeve, near the wearer's temples, for retaining the goggles in place on the user's head. When the elastic strap is tightened, the sleeves press the eye cups firmly against the user's face without the eye cups becoming distorted by stretching under the force of the elastic strap.

36 Claims, 5 Drawing Sheets

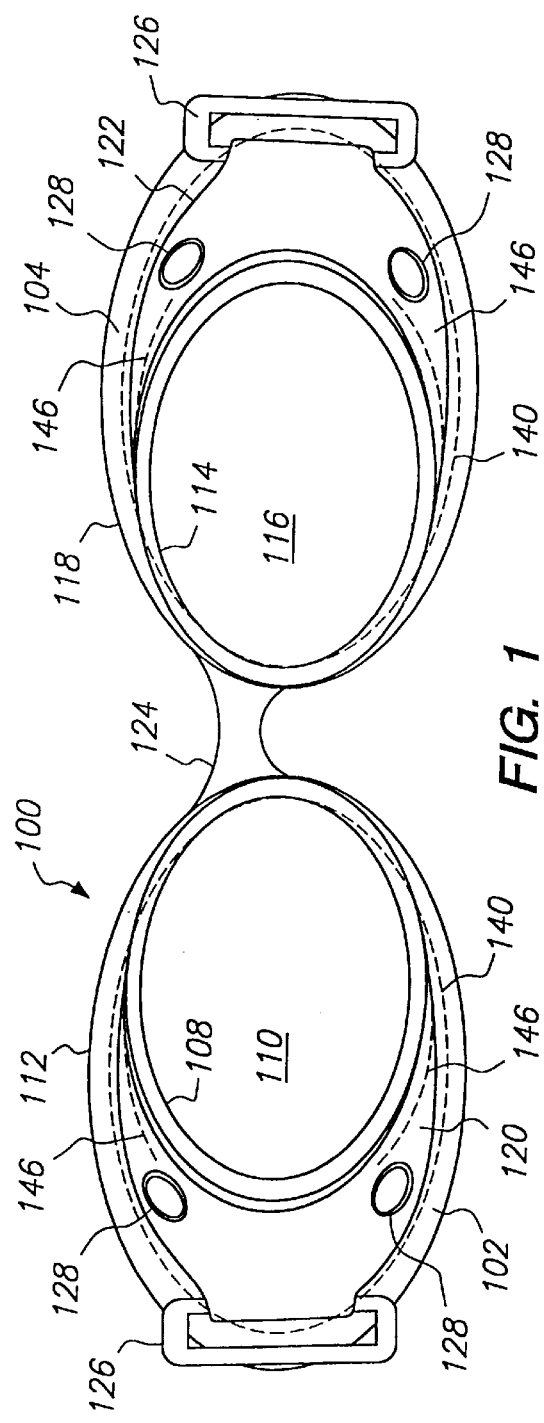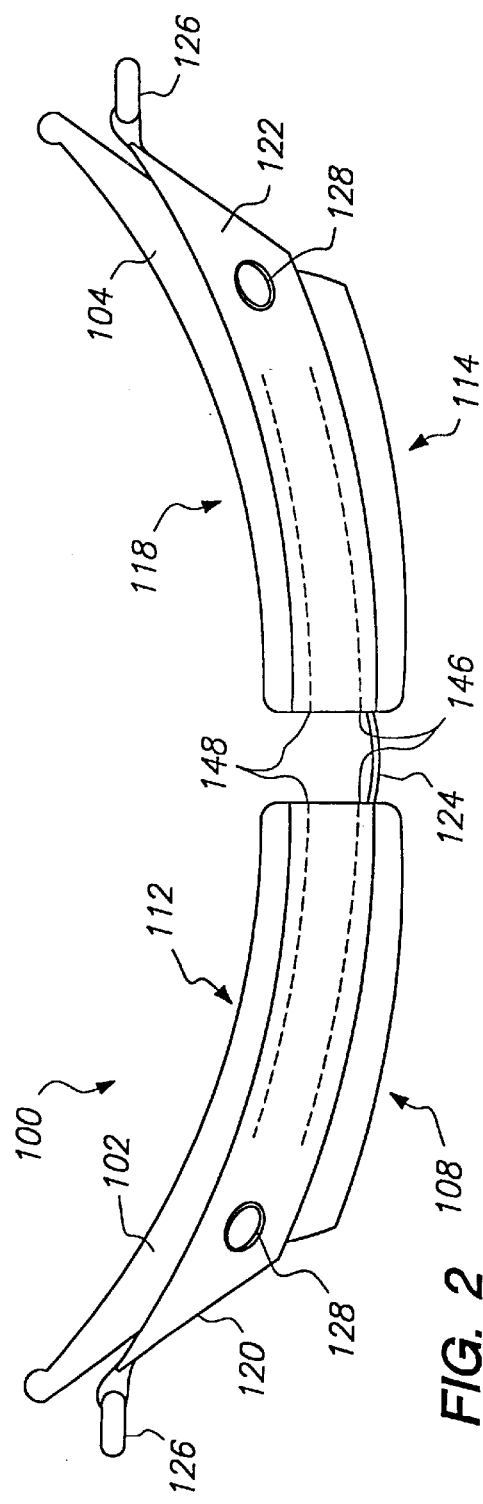

AMPHIBIOUS SPORT GOGGLE HAVING MALLEABLE FRAME AND INTERCHANGEABLE LENSES

FIELD OF THE INVENTION

The invention relates to the field of protective eyewear. More particularly, the invention relates to the field of protective eyewear having a malleable frame and interchangeable lenses for use while engaging in the performance of outdoor activities on land, snow and water.

BACKGROUND OF THE INVENTION

During the performance of many popular outdoor sporting activities, it is desirable, if not imperative, to wear protective eyewear. For example, radiation from the sun can cause glare and can irritate the eye. This effect is exacerbated during the performance of sports performed on the surface of water, such as sailing, windsurfing, water skiing, surfing, wakeboarding and the like, because rays from the sun can reflect from the surface of the water into the eye. In addition, water sprayed into the eye can irritate the eye during the performance of such above-water sports. This is especially true when the water contains sea salt. Sunlight can also be reflected into eye from the surface of snow during the performance of winter sports, such as downhill snow skiing, cross country snow skiing, snowboarding, snowmobiling, mountaineering and the like. Wind can also be a source of discomfort, especially during the performance of fast-moving sports or sports performed in windy or cold climates.

Sunglasses are commonly utilized for protecting the eye from glare, ultraviolet radiation, and other effects of sunlight. Sunglasses typically include a pair of lenses which are held in place in front of the wearer's eyes by a rigid frame. The frame rests upon the wearer's nose and includes pair of rigid members which rest against the sides of the wearer's head and extend over the ears. Sunglasses, however, are not particularly effective at protecting the wearer's eyes from water spray and wind. In addition, during rigorous activities, sunglasses are likely to come off the wearer's head as they are not typically held firmly in place. An elastic strap can be utilized to more firmly attach the sunglasses to the wearer's head. This approach, however, has limited utility in that discomfort may be caused when the rigid frame is pressed more firmly against the wearer's nose and head by such a strap. Sunglasses suffer from another disadvantage in that the frame can become permanently damaged by impact as can occur during the performance of many sports.

Ski goggles are commonly utilized during the performance of winter sports to protect the eyes from the effects of the sun and wind. Ski goggles typically have a single lens attached to a molded plastic frame. The frame is molded such that it conforms to the outline shape of the lens and to a shape of an average wearer's face. The frame is generally sealed to the wearer's face by a piece of foam rubber and is held in place by an elastic strap. Ski goggles are often ill-fitting as they are molded to the face of an average wearer, yet the shape of wearers' faces can vary widely. Also, the molded plastic frame can restrict the wearer's peripheral vision. In addition, ski goggles are prone to becoming fogged in cold climates. Anti-fog coatings are available to alleviate this problem, but they generally do not eliminate it. Further, ski goggles also tend to be relatively large and bulky, making them less aesthetically pleasing and more difficult to carry in a pocket when they are not in use.

Because sunglasses are less protective, but less prone to fogging than ski goggles, persons engaging in winter sports often wear sunglasses when weather conditions are sufficiently mild, but wear ski goggles during more severe weather conditions. Therefore, such persons must have a pair of each, and when unsure of weather conditions, both pairs are kept on hand. This is disadvantageous because the unused pair of sunglasses or ski goggles must be stored, often in the wearer's coat pocket where they are subject to breakage should the wearer fall.

Swim goggles are typically utilized during the performance of water sports which involve the submersion of the wearer's face into the water. Swim goggles are typically constructed of a pair of eye cups which are formed of a transparent hard plastic. The eye cups are held in place by an elastic strap and are sealed to the wearer's face by a rubber seal surrounding each eye cup. Because swim goggles are designed to seal out water while submerged, they tend to seal in moisture. Thus, they are prone to fogging if used during the performance of above-water sports or for land-based sports. In addition, the hard plastic eye cups make such goggles unsuitable for such sports, as they do not yield should the eye cup be impacted during a fall.

Therefore, what is needed is protective eyewear for use while engaging in outdoor activities, especially snow sports and sports performed on the surface of water, which does not suffer from the disadvantages of the protective eyewear commonly utilized while engaging in such sports.

SUMMARY OF THE INVENTION

The invention is an amphibious sport goggle having a malleable frame and interchangeable lenses. The frame includes a pair of eye cups constructed of a soft, flexible and gas permeable material, preferably 4-way stretch "LYCRA" fabric. A lens is held in place across a first open end of each eye cup by pair of flexible rings sewn into the eye cup. The flexible rings are oriented parallel to each other for retaining the lens therebetween. Preferably, the flexible rings are formed of rubber. Because the eye cups and the rings are flexible, the lenses can be easily interchanged with lenses having different shapes, colors and optical properties. Thus, the sport goggle can be easily adapted for use during the performance of many different sports and in a variety weather conditions. Further, the ability to interchange the shape and color of the lenses allows the wearer to adapt the sport goggle to his or her own sense of fashion. A third flexible ring is sewn into each eye cup around the perimeter of a second open end for providing additional structure to the eye cup and for providing a seal between the wearer's face and the eye cup. The third flexible ring is also preferably formed of rubber.

An outer layer forms a sleeve around a portion of each eye cup. The sleeve is attached to the eye cup in the vicinity of the perimeter of the lens. The sleeve is constructed of a durable and flexible material, preferably "CORDURA" fabric. The eye cups are held together near the bridge of the wearer's nose, preferably by a short strap which is attached to each sleeve. An adjustable elastic strap is also attached to each sleeve, near the wearer's temples, for retaining the goggles in place on the wearer's head. When the elastic strap is tightened, the sleeves press the eye cups firmly against the wearer's face without the eye cups becoming distorted by stretching under the force of the elastic strap.

Preferably, at least one vent is provided in each eye cup for aiding in preventing the lenses from becoming fogged. The vent is preferably formed by an eyelet having an opening through its center and which extends through the eye cup and the sleeve.

BRIEF DESCRIPTION OF THE DRAWINGS

FIG. 1 illustrates a front view of a pair of sport goggles according to the present invention.

FIG. 2 illustrates a top view thereof.

DETAILED DESCRIPTION OF A PREFERRED EMBODIMENT

Figure 3:
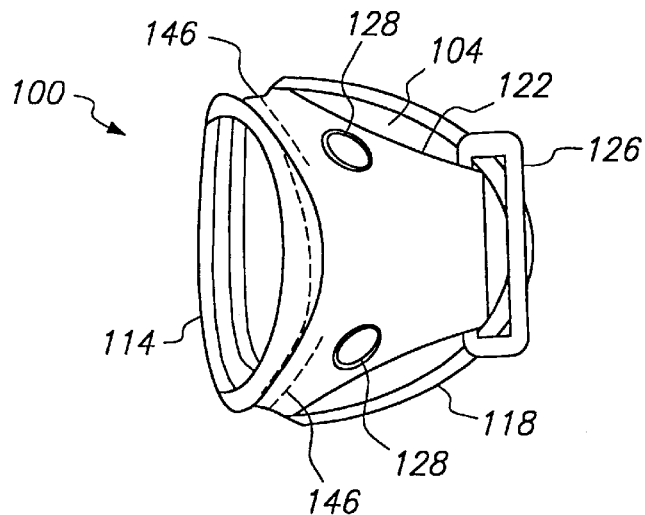
FIG. 3 illustrates a side view thereof.

FIG. 1 illustrates a front view of a pair of sport goggles according to the present invention. FIG. 2 illustrates a top view thereof and FIG. 3 illustrates a side view thereof. Referring to FIGS. 1–3, the sport goggles 100 include a pair of eye cups 102, 104. The eye cup 102 has a first open end 108 which is adapted to accept a lens 110 and a second open end 112 which has a perimeter adapted to conform to the face of a wearer. Similarly, the eye cup 104 has a first open end 114 which is adapted to accept a lens 116 and a second open end 118 which has a perimeter adapted to conform to the face of a wearer. The eye cups 102, 104 are constructed of a flexible and elastic material, preferably 4-way stretch "LYCRA" fabric, but can be constructed of other fabrics or materials, such as "NEOPRENE" fabric, plastic, rubber, foam rubber, or vinyl. Preferably, the material has some rigidity that aids in maintaining the shape of the eye cups 102, 104, and is gas permeable, such that moist air trapped within the eye cups 102, 104 can escape, thereby reducing fogging. In addition, the material preferably can absorb moisture so that the absorbed moisture can conduct heat from the wearer's face to the lens, increasing the temperature of the lens, thereby reducing fogging. Also, the material preferably is elastic so that the eye cups 102, 104 comfortably conform to the wearer's face and conform to the shape of the lenses 110, 116. For these reasons, 4-way stretch "LYCRA" fabric is preferred, but it will be apparent that other materials can be selected based upon the criteria given herein.

As will be explained in more detail herein, the inner cups 102, 104 include flexible, elastic rings which also aid in maintaining the shape of the eye cups 102, 104, allow the eye cups 102, 104 accept various different shaped lenses and which aid in sealing the eye cups 102, 104 to the wearer's face.

The eye cup 102 is partially covered by an outer sleeve 120 and the eye cup 104 is partially covered by an outer sleeve 122. Each sleeve 120, 122 preferably surrounds the eye cup 102, 104 and is attached to the eye cup 102, 104 about the circumference of the eye cup 102, 104 near the first open end 108, 114. Preferably, the sleeves 120, 122 are sewn to the eye cups. The sleeves 120, 122 are attached together by a bridge strap 124.

The sleeve 120 is attached to a clip-ring or D-ring 126 while the sleeve 122 is attached to a clip-ring or D-ring 126. The clip-rings 126 allow a strap 130 (FIG. 4) to be attached to the sport goggles 100 to hold the sport goggles 100 in place on a wearer's head. When the strap 130 is tightened, the sleeves 120, 122 bring the eye cups firmly against the wearer's face. The sleeves 120, 122 are preferably formed of a flexible material such as fabric, plastic, rubber or vinyl, however, because the strap attaches to the sleeves 120, 122 (by attaching to the clip-rings 126), the material is preferably strong and durable and is therefore preferably, "CORDURA" fabric. Alternately, the sleeves 120, 122, can be canvas or nylon fabric. The bridge strap 124 can be made of the same material as the sleeves 120, 122, or can be made of some other material, but is preferably made of an elastic material. In addition, eyelets 128 are preferably provided in the sport goggles 100 to allow moisture to escape from the eye cups 102, 104, thereby reducing fogging.

Figure 4:
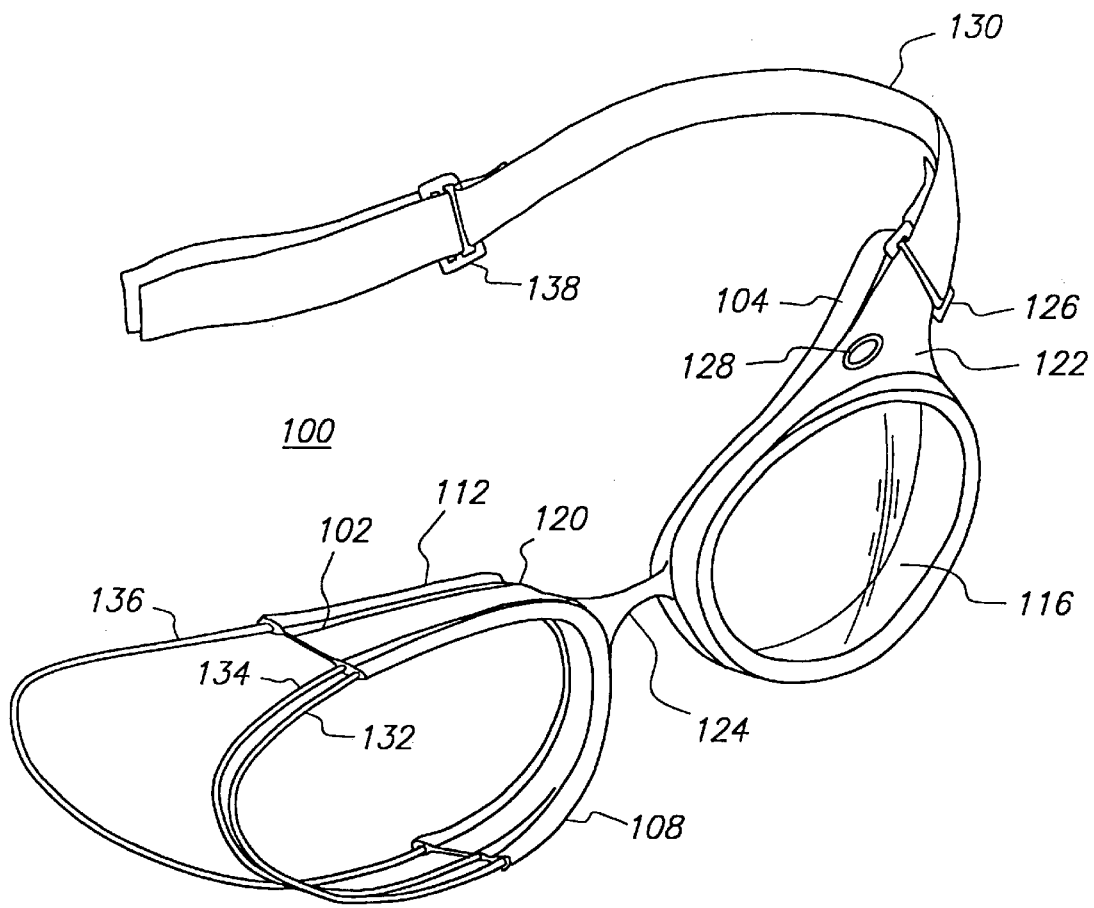
FIG. 4 illustrates a perspective view of the pair of sport goggles according to the present invention with portions removed to show details of construction.

FIG. 4 illustrates a perspective view of the sport goggles according to the present invention with portions removed to show details of construction. In particular, FIG. 4 shows details of the eye cup 102 and strap 130. The eye cup 102 includes an outer ring 132 and an intermediate ring 134 which are sewn into the eye cup 102 across the first open end 108 of the eye cup 102 substantially parallel to each other. The lens 110 (FIG. 1) is held in place between the outer ring 132 and the intermediate ring 134. The eye cup 102 also includes an inner ring 136 which provides additional rigidity around the perimeter of the second open end 112 of the eye cup 102 for providing a seal to the wearer's face when the strap 130 is tightened. Preferably the rings 132, 134, 136 are each formed of a flexible and elastic material, such as rubber or wire.

The ring 132 is preferably sufficiently flexible and large to allow the lens 110 (FIG. 1) to be manually inserted and removed as desired, however, the rings 132, 134 are preferably sufficiently small to prevent the lens 110 from being inadvertently removed. Because the eye cup 102 and rings 132, 134 are flexible, the lens 110 can be replaced with another lens having a different outline shape. In addition, because the cup 102 and rings 132, 134 are elastic, the size of the lens can be altered within the limits of elasticity of the cup 102 and rings 132, 134. The eye cup 102 and the rings 132, 134 will conform to the shape of the new lens. The eye cup 104 is constructed in a like manner to the eye cup 102.

The strap 130 is preferably made of an elastic material and includes an adjustment clip 138 for adjusting the size of the strap 130. When the goggles 100 are worn, the strap 130 pulls on the sleeves 120, 122, which are attached around the circumference of the eye cups 102, 104, near the lenses, rather than directly pulling on the eye cups 102, 104. This arrangement provides several advantages. The eye cups 102, 104 can be made of a material that best suits the functions of the eye cups 102, 104, such as a fabric that is chosen for its softness, comfort, elasticity, moisture absorption and gas permeability, with little regard to its maximum strength and durability, while the sleeves can be made of a material that best suits the functions of the sleeves 120, 122. Thus, the sleeves 120, 122 can be made from a fabric that is chosen for its strength and durability, with little regard to its softness, comfort or elasticity. In addition, when the strap 130 pulls on the sleeves 120, 122, this results in the eye cups 102, 104 being firmly and gently pressed against the wearer's face. Therefore, the inner ring 136 conforms to the unique contours of the wearer's face, comfortably sealing the goggles 100 to the wearer's face. Otherwise, if the tension of the strap 130 was applied directly to the eye cups, 102, 104, this would tend to distort the shape of the inner ring 136, resulting in a less comfortable and less effective seal.

Accordingly, the sleeves 120, 122 are attached to the eye cups 102, 104 in strategic locations to maximize these advantages. Thus, the sleeves 120, 122 are preferably sewn to the eye cups 102, 104 about a circumference of each eye cup 102, 104 that is near the lenses 110, 116. Referring to FIG. 4, the sleeve 120 is preferably sewn to the eye cup 102 around the eye cup 102 in the vicinity of the rings 132 and 134.

For ease of manufacture, the sleeves 120, 122 are preferably also attached to the eye cups 102, 104, by the eyelets 128, as each eyelet 128 preferably extends through the eye cup 102, 104 and the sleeve 120, 122, crimping them together. This feature, however, is not necessary and advantages of the present invention can be achieved without the eyelets attaching the sleeves 120, 122 to the eye cups 102, 104. For example, the eyelets can be made to crimp only to the eye cups 102, 104, or only to the sleeves, 120, 122 with a corresponding opening in the sleeves 120, 122 or eye cups 102, 104 to allow moisture to escape. Alternately, the eyelets 128 can be omitted, or can be replaced with holes, slits or button-holes.

Figure 5A:
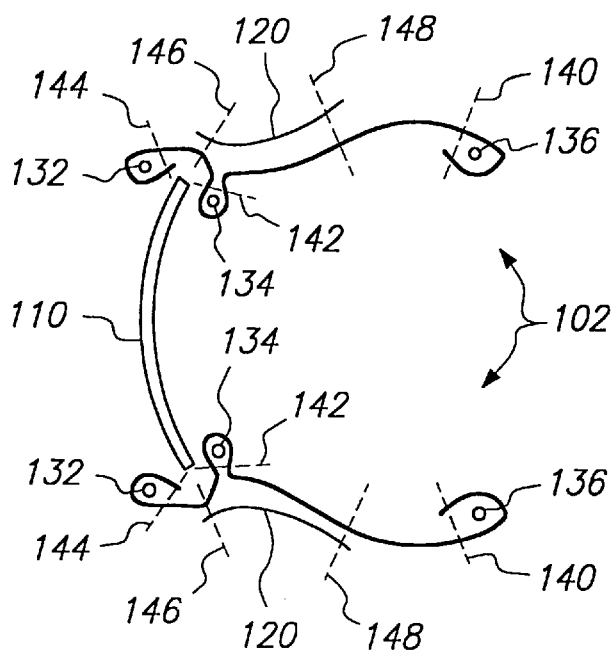
FIG. 5A illustrates a side sectional view of an eye cup of the sport goggles according to the present invention showing stitching details.

FIG. 5A illustrates a side sectional view of the eye cup 102 of the sport goggles 100 showing stitching details. The dotted lines in FIG. 5A represent stitches which extend about the circumference of the eye cup 102 except where noted. The stitches 140 retain the inner ring 136 and are also illustrated in FIG. 1. The stitches 142 retain the intermediate ring 134. The stitches 144 retain the outer ring 132. The stitches 146 secure the sleeve 120 to the eye cup 102 as do the stitches 148. The stitches 146 are preferably located between the rings 132 and 134, but can be located adjacent to either ring or can be located on the opposite side of the ring 134 from the position shown.

The stitches 146 are also illustrated in FIGS. 1–3 while the stitches 148 are illustrated in FIG. 2. The stitches 148 are optional. As illustrated in FIGS. 1–3, the stitches 146 preferably do not extend entirely about the circumference of the eye cup, but instead only extend about approximately 50–60% of the circumference. Therefore, the stitches 146 are not present in the sleeves 120, 122 in an area between each clip-ring 126 and lens 110, 116, but are located on a side of each lens 110, 116 opposite the clip-rings 126. The area where the sleeves 120, 122 are not attached to the eye cups 102, 104 preferably extends between the eyelets 128 of each eye cup 102, 104.

When the goggles are attached to a wearer by the elastic strap 130, this feature prevents the sleeves 120, 122 from pulling directly on the outer portion of the eye cups 102, 104, as would be the case if the elastic strap were to be attached near the wearer's temples. Rather, the force of the elastic strap 130 will be concentrated about the inner portions of the eye cups 102, 104, on a side of each lens 110, 116 opposite the clips 126, and near the bridge strap 124. Therefore, when the elastic strap 130 is tightened, the resulting pressure of the eye cups 102, 104 against the wearer's face is evenly distributed. This prevents the eye cups 102, 104 from becoming distorted under the force of the elastic strap 130 and makes the goggles 100 comfortable to wear over extended periods. Therefore, the eye cups 102, 104 will be able to conform better to the wearer's face and distortion in the eye cups 102, 104 which might dislodge the lenses 110, 116 will be prevented.

Though stitches are preferred, it will be apparent that other attachment methods, such as adhesive bonding, can be utilized. Further, the eye cups 102, 104 can be made of a single piece of appropriately formed material, such as rubber.

Figure 5B:
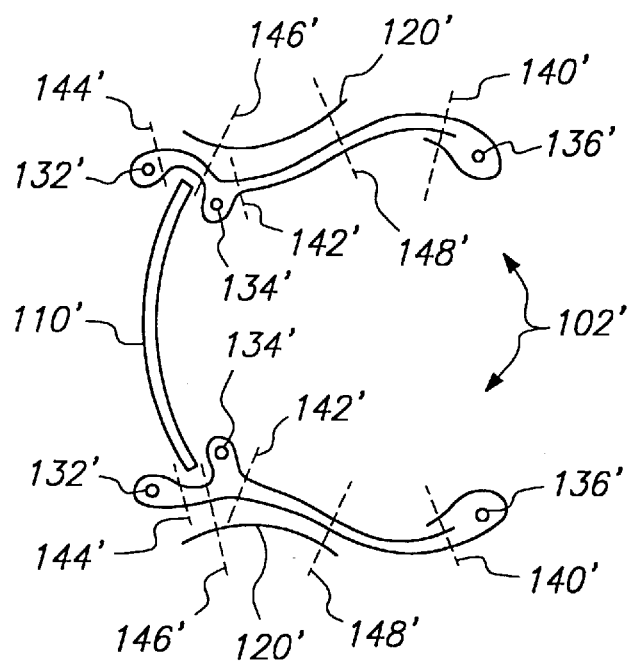
FIG. 5B illustrates a side sectional view of an eye cup of the sport goggles according to the present invention showing preferred stitching details.
Figure 6A:
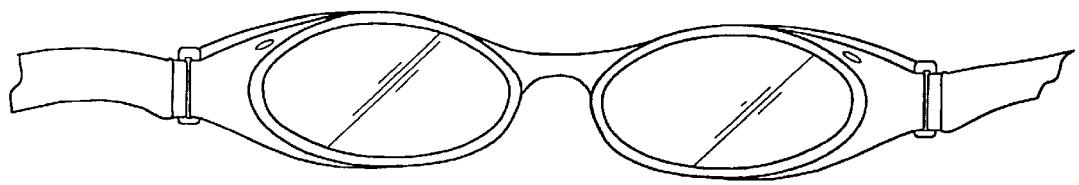
FIGS. 6A through 6D illustrate the sport goggles according to the present invention having lenses of various different outline shapes.
Figure 6B:
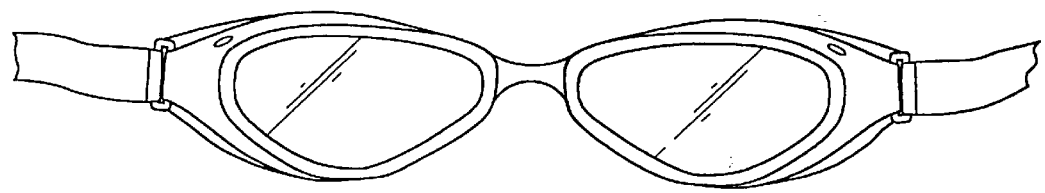
Figure 6C:
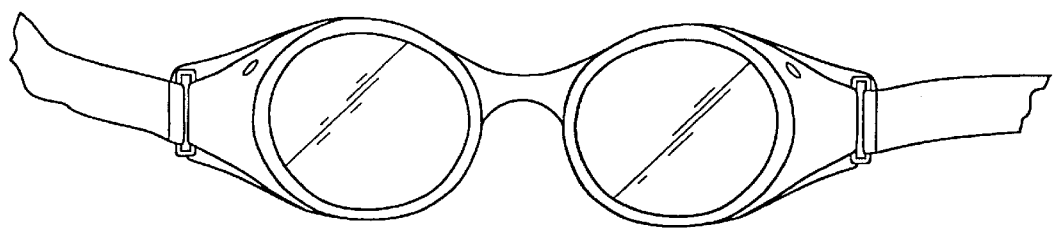
Figure 6D:
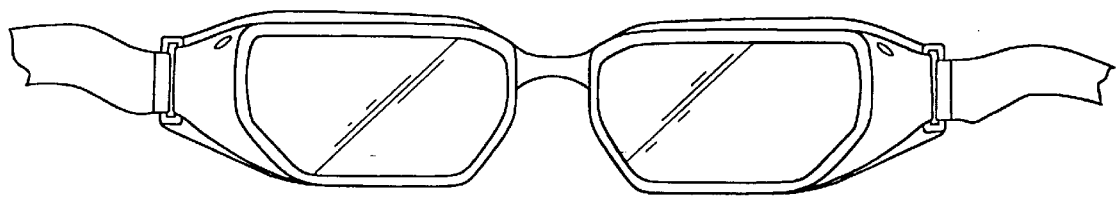

FIG. 5B illustrates a side sectional view of an eye cup 102' of the sport goggles according to the present invention showing preferred stitching details. Stitching elements of FIG. 5B having a one-to-one functional correspondence to stitching elements of FIG. 5A are identified with primed reference characters. Accordingly, the dotted lines in FIG. 5B represent stitches which extend about the circumference of the eye cup 102' except where noted. The stitches 142' retain the intermediate ring 134'. The stitches 144' retain the outer ring 132'. The stitches 146' secure the sleeve 120' to the eye cup 102' as do the stitches 148'. The stitches 146' are preferably located between the rings 132' and 134', but can be located adjacent to either ring or can be located on the opposite side of the ring 134' from the position shown. The stitches 148' are optional. And, like the stitches 146 illustrated in FIG. 5A, the stitches 146' preferably do not extend entirely about the circumference of the eye cup.

FIGS. 6A through 6D illustrate the sport goggles 100 according to the present invention having lenses of various different outline shapes installed. FIGS. 6A through 6D illustrate that the appearance of the goggles and the shape of the eye cups can change dramatically by changing only the lenses. It will be apparent that the shape of the lenses can be oval, teardrop, round, hexagonal, octagonal, or another closed figure formed of straight or curved lines. The appearance of the goggles can also be altered by rotating the lenses within the eye cups. The variety of possible outline shapes for the lenses are limited only in that the eye cups 102, 104 should be able to conform to the lenses without gaps between the lenses and eye cups 102, 104 which could allow unfiltered light to enter the wearer's eye. It will be apparent that the lenses can have a variety of different optical properties, such as different colors of tint, darkness of tint, or reflective coatings, and can even be corrective lenses. If desired, the material utilized to form the eye cups 102, 104, the sleeves 120, 122, or strap 130 can be of various colors or patterns.

Figure 7:
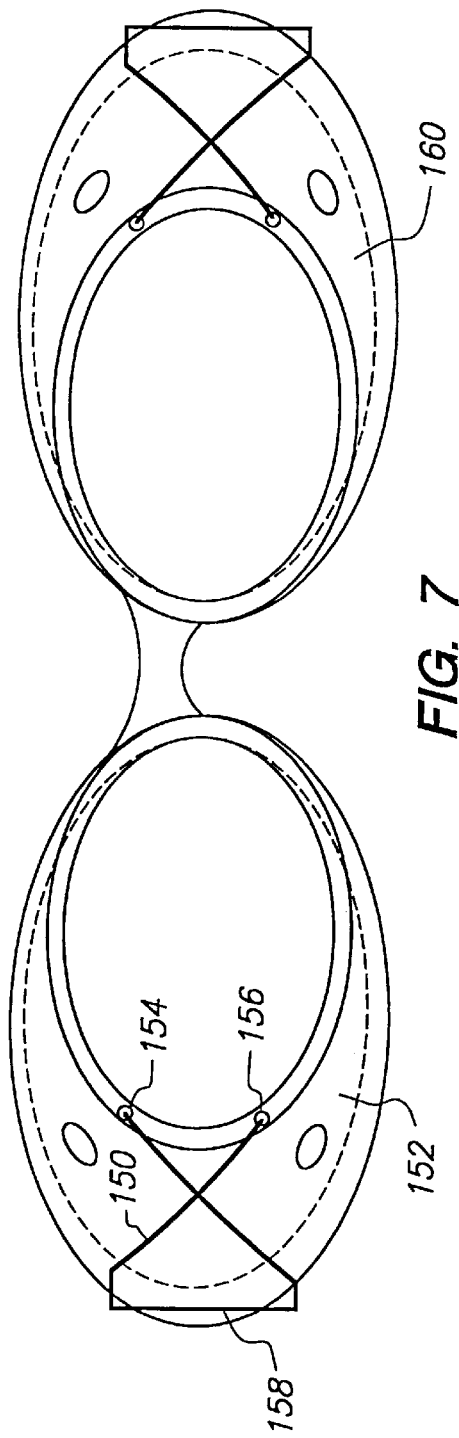
FIG. 7 illustrates a first alternate embodiment of the present invention having a cinching lens mount.

FIG. 7 illustrates a first alternate embodiment of the present invention wherein the outer ring 132 is replaced with a cinching lens mount 150. The cinching lens mount 150 is preferably formed of wire, but can be formed of another material, such as plastic or rubber. The cinching lens mount 150 has an oval portion which is sewn into the eye cup 152. Two openings 154, 156 are provided in the eye cup 152 for the cinching lens mount 150 to exit the eye cup 152. Once the cinching lens mount 150 exits the openings 154, 156, it preferably crosses itself and the ends are coupled together, forming a loop 158. It will be apparent, however, that the cinching lens mount 150 need not cross itself. A second eye cup 160 is constructed in a like manner. A strap can be attached to the loop 158 for holding the goggles in place on the wearer's head. As the strap is tightened, the oval portion of the cinching lens mount 150 will tend to constrict, thus securing the lens in place. Note that in this embodiment, an outer sleeve, such as the sleeve 120, is not required.

Figure 8:
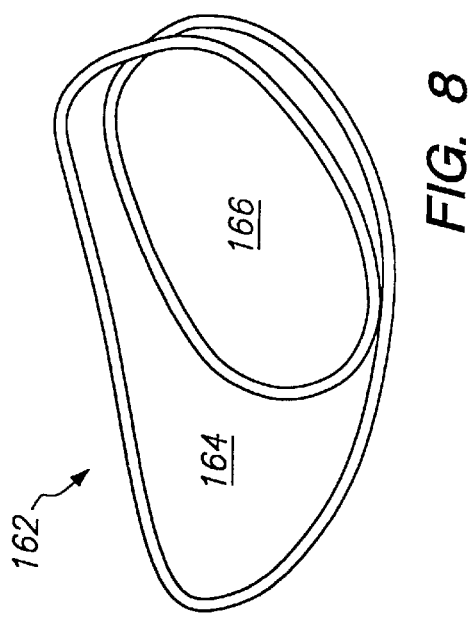
FIG. 8 illustrates a single overlapping ring of a second alternate embodiment of the present invention.

FIG. 8 illustrates a single overlapping ring 162 of a second alternate embodiment of the present invention for replacing the intermediate ring 134 and inner ring 136. The overlapping ring 150 illustrated in FIG. 8 is drawn to contrast with the intermediate ring 134 and inner ring 136 of FIG. 4. It will be apparent that the overlapping ring 162 provides additional structure for the eye cup, as do the rings 134 and 136. The overlapping ring 162 forms a loop 166 which serves to hold the lens in place by replacing the intermediate ring 134 and the overlapping ring 162 forms a loop 164 which conforms to the wearer's face by replacing the inner ring 136. The embodiment illustrated in FIG. 8 can include an outer ring 132, as illustrated in FIG. 4, or a cinching lens mount 150, as illustrated in FIG. 7, to retain the lens.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention. Specifically, it will be apparent to one of ordinary skill in the art that the device of the present invention could be implemented in several different ways and the apparatus disclosed above is only illustrative of the preferred embodiment of the invention and is in no way a limitation.

What is claimed is:

1. Eyewear comprising:
   a. an eye cup having a first open end adapted for retaining a first lens therein and a second open end having a perimeter adapted for conforming to a wearer's face, wherein the first open end is adapted to retain a second lens therein having an outline shape different from the first lens;
   b. first and second elastic rings parallely attached to the first open end for removably retaining the first or second lens therebetween; and
   c. a third elastic ring attached to the perimeter of the second open end wherein the third elastic ring conforms to the wearer's face.

2. The eyewear according to claim 1 wherein the eye cup elastically conforms to the outline shape of the first and second lenses.

3. The eyewear according to claim 1 wherein a rotational orientation of the first lens relative to the eye cup is selectable.

4. The eyewear according to claim 1 further comprising an elastic strap attached to the first elastic ring for retaining the eyewear on the wearer's face wherein the first elastic ring is configured to cinch the first open end when the elastic strap is tightened on the wearer.

5. The eyewear according to claim 1 wherein the eye cup comprises a first ring and an overlapping ring, wherein the overlapping ring has first and second loops and wherein the first ring and first loop are parallely attached to the first open end for retaining a lens therebetween and the second loop is attached to the perimeter of the second open end for conforming to a wearer's face.

6. Eyewear comprising:
   a. an eye cup having a first open end adapted for retaining a lens and a second open end having a perimeter adapted for conforming to a wearer's face;
   b. a sleeve surrounding a portion of the eye cup and attached to the eye cup about at least a portion of a circumference of the eye cup adjacent to the first open end; and
   c. a strap for retaining the eyewear to the wearer's face wherein the strap is attached to the sleeve.

7. The eyewear according to claim 6 wherein the portion of the circumference of the eyecup attached to the sleeve is located on an opposite side of the first open end from a location of attachment of the strap to the sleeve.

8. The eyewear according to claim 7 wherein the sleeve is not attached to the eyecup in an area between the first open end and the location of attachment of the strap to the sleeve.

9. The eyewear according to claim 6 wherein first open end is adapted to removably accept another lens having a different outline shape.

10. The eyewear according to claim 8 wherein first and second elastic rings are parallely attached to the first open end for removably retaining the lens therebetween.

11. The eyewear according to claim 10 wherein a third elastic ring is attached to the perimeter of the second open end.

12. The eyewear according to claim 8 wherein the eye cup is constructed of an elastic material.

13. The eyewear according to claim 12 wherein the sleeve is constructed of a material that is less elastic than the eye cup.

14. The eyewear according to claim 13 wherein the eye cup is formed of stretchable fabric and the sleeve is formed of canvas fabric.

15. Eyewear comprising:
   a. a flexible eye cup having a first open end and a second open end, wherein first and second flexible rings are parallely attached to the first open end for retaining a lens therebetween and across the first open end; and
   b. a third flexible ring attached to the second open end, wherein the third ring is adapted for conforming to a wearer's face.

16. The eyewear according to claim 15 wherein first open end is adapted to removably accept another lens having a different outline shape.

17. The eyewear according to claim 15 wherein a rotational orientation of the lens relative to the eye cup is selectable.

18. The eyewear according to claim 16 wherein the eye cup elastically conforms to the outline shape of the first and second lenses.

19. Eyewear comprising an eye cup having a first open end adapted for retaining a first lens therein and a second open end having a perimeter adapted for conforming to a wearer's face, wherein the first open end is adapted to retain a second lens having a different outline shape than the first lens and further wherein the eye cup comprises a first ring and an overlapping ring, wherein the overlapping ring has first and second loops and wherein the first ring and first loop are parallely attached to the first open end for retaining a lens therebetween and the second loop is attached to the perimeter of the second open end for conforming to a wearer's face.

20. Eyewear comprising:
   a. an eye cup having a first open end adapted for retaining a first lens therein and a second open end having a perimeter adapted for conforming to a wearer's face, wherein the first open end is adapted to retain a second lens therein having an outline shape different from the first lens;
   b. a sleeve surrounding a portion of the eye cup and attached to the eye cup about at least a portion of a circumference of the eye cup; and
   c. a strap for retaining the eyewear to the wearer's face.

21. The eyewear according to claim 20 wherein the strap is attached only to the sleeve.

22. The eyewear according to claim 21 wherein the portion of the circumference of the eye cup attached to the sleeve is located on an opposite side of the first open end from a location of attachment of the strap to the sleeve.

23. The eyewear according to claim 22 wherein the sleeve is not attached to the eye cup in an area between the first open end and the location of attachment of the strap to the sleeve.

24. The eyewear according to claim 20 wherein first and second elastic rings are parallely attached to the first open end for removably retaining the first or second lens therebetween.

25. The eyewear according to claim 24 wherein a third flexible ring is attached to the perimeter of the second open end.

26. The eyewear according to claim 20 wherein the eye cup is constructed of an elastic material.

27. The eyewear according to claim 26 wherein the sleeve is constructed of a material that is less elastic than the eye cup.

28. The eyewear according to claim 20 wherein when the strap is tightened on the wearer, force of the strap is distributed so as to prevent the eye cup from distorting under force of the strap.

29. Eyewear comprising:
   a. a first eye cup having a first open end adapted for retaining a first lens therein and a second open end having a perimeter adapted for conforming to a wearer's face, wherein the first open end of the first eye cup is adapted to retain a second lens therein having an outline shape different from the first lens;
   b. a second eye cup having a first open end adapted for retaining a third lens therein and a second open end having a perimeter adapted for conforming to the wearer's face, wherein the first open end of the second eye cup is adapted to retain a fourth lens therein having an outline shape different from the third lens; and
   b. a flexible bridge strap attached to each of the first and second eye cups whereby the first and second eye cups are jointedly articulable with respect to one another.

30. The eyewear according to claim 29 wherein the first eye cup elastically conforms to the outline shape of the first and second lenses.

31. The eyewear according to claim 29 wherein a rotational orientation of the first lens relative to the first eye cup is selectable.

32. The eyewear according to claim 29 wherein first and second elastic rings are attached to the first open end of the first eye cup for removably retaining the first or second lens therebetween.

33. The eyewear according to claim 32 further comprising an elastic strap attached to the first elastic ring for retaining the eyewear on the wearer's face wherein the first elastic ring is configured to cinch the first open end when the elastic strap is tightened on the wearer.

34. The eyewear according to claim 32 wherein a third flexible ring is attached to the perimeter of the second open end of the first eye cup wherein the third flexible ring conforms to the wearer's face.

35. The eyewear according to claim 29 wherein the first eye cup comprises a first ring and an overlapping ring, wherein the overlapping ring has first and second loops and wherein the first ring and first loop are parallely attached to the first open end of the first eye cup for retaining a lens therebetween and the second loop is attached to the perimeter of the second open end of the first eye cup for conforming to a wearer's face.

36. The eyewear according to claim 29 further comprising an elastic strap for retaining the eyewear on the wearer's face wherein when the elastic strap is tightened on the wearer, force of the strap is distributed so as to prevent the eye cup from distorting under force of the elastic strap.

* * * * *